(12) United States Patent
Alepee et al.

(10) Patent No.: US 9,228,967 B2
(45) Date of Patent: Jan. 5, 2016

(54) MICRO-HOTPLATE DEVICE AND SENSOR COMPRISING SUCH MICRO-HOTPLATE DEVICE

(71) Applicant: SGX SENSORTECH SA, Corcelles (CH)

(72) Inventors: Christine Alepee, Fontaines (CH); Nicolas Moser, Chezard-St-Martin (CH)

(73) Assignee: SGX SENSORTECH SA, Corcelles (CH)

( * ) Notice: Subject to any disclaimer, the term of this patent is extended or adjusted under 35 U.S.C. 154(b) by 0 days.

(21) Appl. No.: 14/414,068

(22) PCT Filed: Jul. 16, 2013

(86) PCT No.: PCT/EP2013/065037
§ 371 (c)(1),
(2) Date: Jan. 9, 2015

(87) PCT Pub. No.: WO2014/012948
PCT Pub. Date: Jan. 23, 2014

(65) Prior Publication Data
US 2015/0212030 A1    Jul. 30, 2015

(30) Foreign Application Priority Data

Jul. 16, 2012  (WO) ................. PCT/EP2012/063931

(51) Int. Cl.
*G01N 15/06*       (2006.01)
*G01N 33/00*       (2006.01)
(Continued)

(52) U.S. Cl.
CPC .............. *G01N 27/128* (2013.01); *G01N 27/18* (2013.01)

(58) Field of Classification Search
CPC ........ G01N 15/06; G01N 33/00; G01N 33/48
USPC ............. 422/50, 83, 84, 82.01, 82.02, 94, 95, 422/96, 97, 98; 436/43, 147, 181
See application file for complete search history.

(56) References Cited

U.S. PATENT DOCUMENTS 7,862,233 B2 *  1/2011  Hyde et al. ..................... 374/178
8,931,950 B2 *  1/2015  King et al. ...................... 374/36
(Continued)

FOREIGN PATENT DOCUMENTS

EP         0859536 A1     8/1998
EP         1273908 A1     1/2003
(Continued)

OTHER PUBLICATIONS

International Search Report for PCT/EP2013/065037 mailed Oct. 15, 2013.
(Continued)

*Primary Examiner* — Brian J Sines
(74) *Attorney, Agent, or Firm* — Koppel, Patrick, Heybl & Philpott (57) ABSTRACT

The present invention relates to a micro-hotplate device comprising a frame, a membrane, an active area comprising at least one active layer, and a heating structure designed to heat said active layer, said heating structure having concentric tracks and comprising inner tracks (20) and inner spaces (22) and outer tracks (24) and outer spaces (26) as being the one or two tracks and spaces located the furthest away from the center of the heating structure, characterized in that said outer tracks (24) are designed to be located closer to their neighboring tracks and/or are designed to have a width which is lower than those of the inner tracks (20), the width and the spacing of said inner tracks (20) being substantially constant.

24 Claims, 4 Drawing Sheets

(51) Int. Cl.
*G01N 33/48* (2006.01)
*G01N 27/12* (2006.01)
*G01N 27/18* (2006.01)

(56) References Cited

U.S. PATENT DOCUMENTS

| | | |
|---|---|---|
| 2004/0093928 A1 | 5/2004 | DiMeo |
| 2004/0118202 A1 | 6/2004 | Iwaki |
| 2005/0121630 A1 | 6/2005 | Arndt |
| 2008/0179713 A1* | 7/2008 | Landsberger et al. ........ 257/633 |
| 2011/0174799 A1 | 7/2011 | Ali |

FOREIGN PATENT DOCUMENTS

| | | |
|---|---|---|
| EP | 2278308 | 1/2011 |
| GB | 2464016 A | 4/2010 |
| WO | WO 0075649 A1 | 12/2000 |
| WO | WO 02/50528 A1 | 6/2002 |
| WO | WO 02080620 A1 | 10/2002 |
| WO | WO 2007026177 | 3/2007 |

OTHER PUBLICATIONS

Iwaki T et al: 11 Design and simulation of 1-23 resistive SOI CMOS micro-heaters for high temperature gas sensors~~. Journal of Physics: Conference Series. Institute of Physics Publishing. Bristol. GB. vol. 15. No. 1. Jan. 1, 2005. pp. 27-32. XP020093800. ISSN: 1742-6596. DOI: 10.1088/1742-6596/15/1/005 p. 28. 1 i ne 15. paragraph 4-line 20; figures 1.2.

Lees M et al: "Design and optimization of a high-temperature silicon micro-hotplate for nanoporous palladium pellistors". Microelectronics Journal. Mackintosh Publications Ltd. Luton. GB. vol. 1 • 34. No. 2. Feb. 1, 2003. pp. 115-126. XP004404380. ISSN: 0026-2692. DOI: 10.1016/S0026-2692(02)00153-2 p. 119. paragraph 4.1-paragraph 4.2; figures 2.4.

I Elmi, et al. "Optimization of a wafer-leel process for the fabrication of highly reproducible thin-film MOX sensors", CNR-IMM Bologna, Vta P. Gobetti 101, 40129 Bologna, Italy Received Nov. 27, 2006; received in revised form Dec. 13, 2007; accepted Dec. 14, 2007 Available online Feb. 19, 2008, Elsevier, Sensors and Actuators B 131 (2008) 548-555.

Dae-Sik Lee, et al. "Fabrication and characterization of micro-gas sensor for nitrogen oxides gas detection", School of Electronic and Electrical Engineering, Kyungpook National University, Taegu 702-701, South Korea b Department of Metallugical Engineering, Kyungpook National University, Taegu 702-701, South Korea, Elsebier, Sensors and Actuators B 64 (2000) 31-36.

Markus Graf, et al. "CMOS micro hotplate sensor system for operating temperatures up to 500 C", ETH Zurich, Physical Electronics wboratory, HPT-H8, CH-8093 Zurich, Switzerland Received Aug. 9, 2005; accepted Nov. 7, 2005 Available online Jan. 18, 2006, Elsevier, Sensors and Actuators B 117 (2006) 346-352.

International Report and Written Opinion from corresponding Appl. No. PCT/EP2013/065037. dated Jan. 20, 2015.

* cited by examiner

MICRO-HOTPLATE DEVICE AND SENSOR COMPRISING SUCH MICRO-HOTPLATE DEVICE

TECHNICAL FIELD

The present invention relates to a micro-hotplate device. The present invention relates also to sensors comprising such micro-hotplate device, said sensors being more specifically gas sensor devices.

BACKGROUND OF THE INVENTION

MEMS-based micro-hotplates are more and more often used in applications such as miniature flow sensors or gas sensors, the detection principle of which is relying on the temperature elevation of the surrounding gas and/or of an active functional layer. The small size of these micro-sensors offers advantages when integrating in portable devices. However, in such applications not only the small size but also the low power consumption is a key parameter because of its direct consequence on battery lifetime of the portable instrument. For this reason, significant research and development has been carried out, aiming to maximize the efficiency of these sensors, i.e. to maximize sensitivity, selectivity, stability, and speed of response while minimizing the power consumption of the micro-hotplate.

Micro-hotplates are typically based on a membrane structure extending across a rigid frame, on which a resistive heating structure is deposited in order to heat the active area of the membrane to a given desired temperature. The temperature uniformity of the active area is a critical factor for good sensor efficiency, i.e. for an optimum usage of the consumed power which has to be kept as low as possible.

The temperature uniformity can be optimized by using an appropriate pattern for the heating structure.

Figure 1:
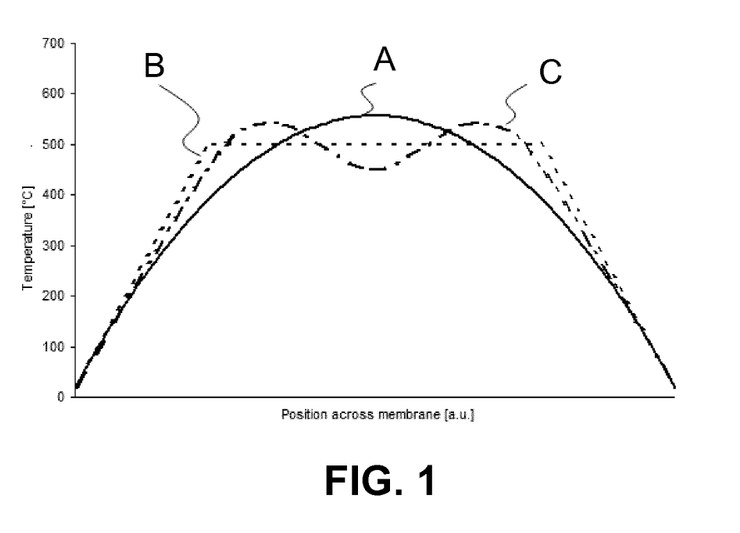
FIG. 1 represents the temperature as a function of the position across the membrane for different patterns of heating structures of the prior art compared to an ideally sought temperature profile.

The most common and straightforward heating resistor pattern used for micro-hotplates is a simple meander of constant width and constantly spaced tracks as illustrated e.g. in EP 0859536 or WO 02/080620. This type of heater represents a nearly uniform heat source but yields a non-uniform temperature distribution due to the conductive heat losses through the membrane to the cold frame. FIG. 1 shows the type of temperature profile obtained across a micro-hotplate by using a uniform heat source (Curve A) compared with the ideally sought uniform temperature profile (Curve B) in the active area (with a target temperature of 500° C. in this example).

In order to correct this lack of temperature uniformity, two strategies have been investigated principally:
  to increase the thermal conductivity within the active area by the use of an additional heat spreading plate in order to locally facilitate heat transfer by conduction in the plane of the membrane and thus reduce temperature gradients in the active area;
  to locally tune the dissipated heat by varying the heater's section and/or its location.

The heat spreading plates of the first strategy can be for example silicon islands located underneath the membrane (e.g. WO 00/75649 or "CMOS microhotplate sensor system for operating temperatures up to 500° C." by Graf et al., Sensors and Actuators B 117 (2006) 346-352) or an additional metal plate located between two dielectric layers between the heater and the active layer (e.g. GB 2464016). This approach reduces more or less efficiently the temperature gradients in the active area, depending on the thermal conductance of the heat spreading plate. However, in any case, the fabrication of this additional heat spreading plate represents a considerable increase in the process complexity, the number of process steps, as well as the risks linked to thermo-mechanical stresses in multiple-layer structures working at high temperatures. Also, this heat spreading plate represents an additional thermal mass that increases the thermal inertia of the micro-hotplate and hence also its thermal response time which is a major drawback for applications where these hotplates are used in cycle mode, e.g. when they are used as IR emitters in IR absorption gas sensors.

The second strategy does not present these drawbacks as it only looks to vary the shape of an already present layer and thus does not require any additional layer, neither any additional process step and also does not increase the thermal mass of the volume to be heated. Various empirical attempts have been made to improve the temperature uniformity of micro-hotplates by local tuning of the dissipated heat. One approach consists in creating one or more hollows in the heater tracks (e.g. EP 1273908, or US 2004/118202) in order to locally, in the hollow, suppress the heat source and in the same time increase the heat dissipation at the borders of the hollow due to the local forced concentration of the current lines. Another approach consists in heating only the periphery of the active area (see for example U.S. Pat. No. 7,279,692 or "Fabrication and characterization of micro-gas sensor for nitrogen oxides gas detection" by Lee et al./Sensors and Actuators B 64 (2000) 31-36). Both of these two first approaches yield typically temperature profiles with a more or less important temperature drop in the non-heated center like illustrated by Curve C in FIG. 1. Other approaches consist in varying the track's section by decreasing progressively the track width from the center to the border of a snail-shaped heater track (EP 2278308) or, to the opposite, by increasing this track width towards the border of the active area (WO 2007/026177). Other designs also combine a variable track width with variable track spacing ("Optimization of a wafer-level process for the fabrication of highly reproducible thin-film MOX sensors" by Elmi et al., Sensors and Actuators B 131 (2008) 548-555). All these very different and even partly contradictory solutions as well as studies like "Design and optimization of a high-temperature silicon micro-hotplate for nanoporous palladium pellistors" (Lee et al. Microelectronics Journal 34 (2003) 115-126) illustrate well the empirical trial and error method used to design these micro-hotplate heaters.

Therefore there are, at the present time, no adequate solutions, for obtaining good temperature uniformity in the active area of the micro-hotplates in order to increase the accuracy, efficiency, and reliability of the sensors using such micro-hotplates.

SUMMARY OF THE INVENTION

The present invention provides a micro-hotplate device which allows to avoid the disadvantages of the prior art.

Accordingly, the present invention relates to a micro-hotplate device comprising a frame, a membrane, an active area comprising at least one active layer, and a heating structure designed to heat said active layer, said heating structure having concentric tracks and comprising inner tracks and inner spaces and outer tracks and outer spaces as being the one or two tracks and spaces located the furthest away from the center of the heating structure, said outer tracks being designed to be located closer to their neighboring tracks and/or being designed to have a width which is lower than those of the inner tracks, such that said outer tracks are narrower than the inner tracks, the width and the spacing of said inner tracks being substantially constant.

Such design of the heating structure guarantees optimum temperature uniformity in the active area of micro-hotplates.

The present invention relates also to a gas sensor comprising such a micro-hotplate device.

The present invention relates also to a catalytic gas sensor comprising such a micro-hotplate device.

The present invention relates also to an infrared-absorption gas sensor comprising such a micro-hotplate device.

The present invention relates also to a chemoresistive gas sensor comprising such a micro-hotplate device.

The present invention relates also to a method for measuring a concentration of a gas by using a gas sensor comprising a micro-hotplate device as disclosed above, such micro-hotplate device having a heating structure to which at least one heating voltage or at least one heating current is applied to heat the active layer and allow measurement of a concentration of said gas, said at least one heating voltage or said at least one heating current being supplied intermittently in cycle mode.

DETAILED DESCRIPTION

Figure 2:
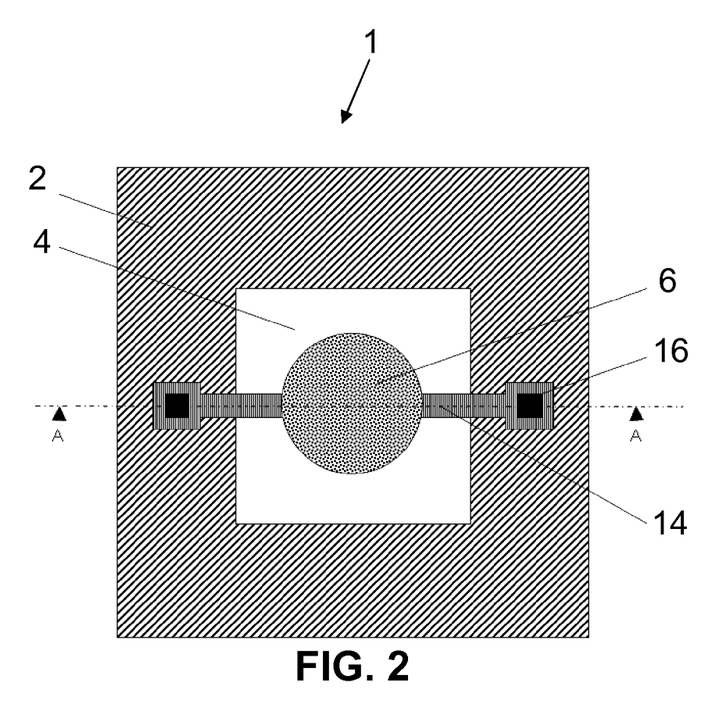
FIG. 2 represents a schematic top view of a micro-hotplate device according to the invention.
Figure 3:
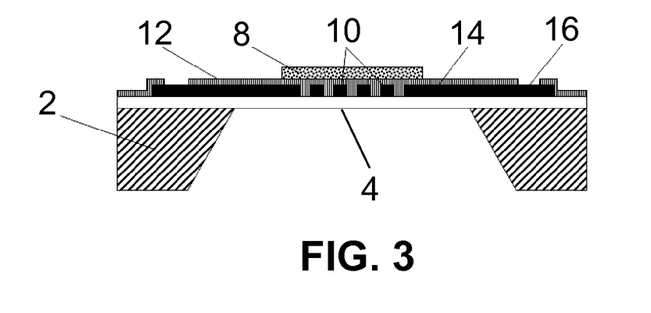
FIG. 3 is a A-A cross-section view of the micro-hotplate device of FIG. 2, FIGS. 4a to 4d show top views of patterns of heating structures used in the invention.

Referring to FIGS. 2 and 3, the micro-hotplate device 1 of the invention comprises:
a rigid frame 2,
a membrane 4 extending across said rigid frame 2,
an independent (i.e. electrically not connected) active area 6 comprising at least one active layer 8,
a heating structure 10 which is deposited on the membrane 4 and designed to heat said active layer 8 to a given desired temperature,
a dielectric layer 12 for insulating the active layer from the heating structure, and
contact tracks 14 and bonding pads 16 for connecting the heating structure 10.

Said micro-hotplates are used in sensors, and more particularly in gas sensors. Depending on the sensor type, various combinations of passive and active layers can be deposited on top of the heating structure to achieve the functionality of the sensor.

The lateral dimensions of the membrane 4 are typically in the range of 100 μm to a few mm, whereas its thickness ranges typically from 100 nm to a few μm. The membrane material is usually as insulating as possible from a thermal point of view in order to limit heat losses by conduction from the heat source to the "cold" frame through the membrane 4.

As shown by FIGS. 4a-4d, the heating structure 10 has concentric tracks and comprises inner tracks 20 and inner spaces 22 and outer tracks 24 and outer spaces 26 as being the one or two tracks and spaces located the furthest away from the center of the heating structure 10.

According to the invention, said outer tracks 24 are designed to be located closer to their neighboring tracks and/or are designed to have a width which is lower than those of the inner tracks 20, such that said outer tracks 24 are narrower than the inner tracks 20, the width and the spacing of said inner tracks 20 being substantially constant.

In the present description, the term "substantially constant" means that the width and spacing of the inner tracks do not differ by more than 20%. This also means that the difference between the width of the outer spaces and the width of the inner spaces is greater than 20% and/or that the difference between the width of the outer tracks and the width of the inner tracks is greater than 20%.

With such heating structure, the heat source is uniform within the active area where it compensates for the uniform heat losses by convection and radiation and is increased at the border of the active area in order to compensate for the additional heat losses by conduction through the membrane to the cold frame, in such a way that equilibrium with a uniform temperature in the active area is reached.

The embodiment for which the outer tracks 24 are designed to be narrower than the inner tracks 20 is more particularly used for outer tracks 24 which are connected in series with each other and with the inner tracks 20.

The optimum "inner space width/outer space width" and "inner track width/outer track width" ratios are not fixed. They depend on the ratio between the convection and radiation losses at the target temperature and the conductive losses through the membrane for this same active area temperature. They are also determined by the minimum space and track width definable by the used patterning technology.

Preferably, when the outer tracks 24 are designed to be located closer to their neighboring tracks, the ratio inner space width/outer space width is higher than 2, and more preferably higher than 4. Preferably also, the ratio inner space width/outer space width is less than 50.

Preferably, when the outer tracks 24 are designed to have a width which is lower than those of the inner tracks 20, the ratio inner track width/outer track width is higher than 1.3, and more preferably higher than 2. Preferably also, the ratio inner track width/outer track width is less than 5.

Figure 4A:
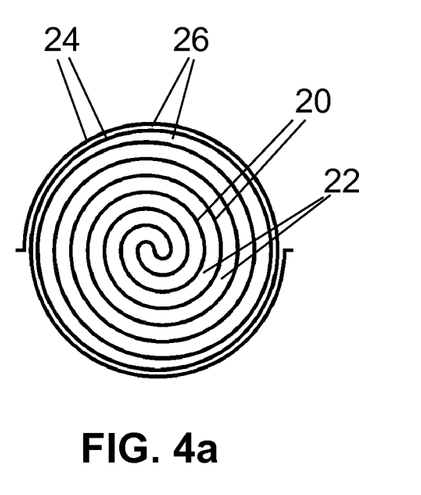
Figure 4B:
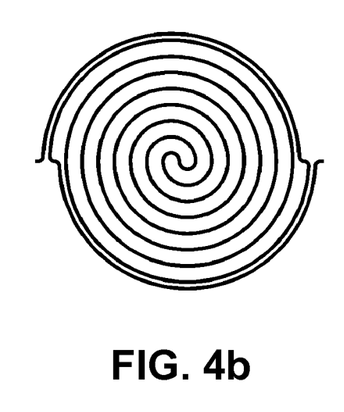
Figure 4C:
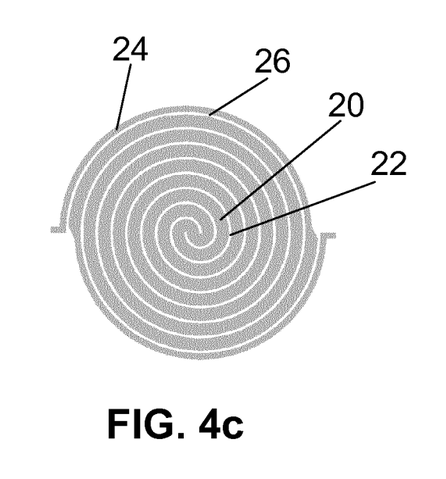

In some preferred embodiments, the tracks may be circular, as shown by FIGS. 4a to 4c.

More particularly, FIGS. 4a and 4b shows heating structure in which the outer tracks 24 are located closer to their neighboring tracks, the ratio inner space width/outer space width being about 4.

Figure 4D:
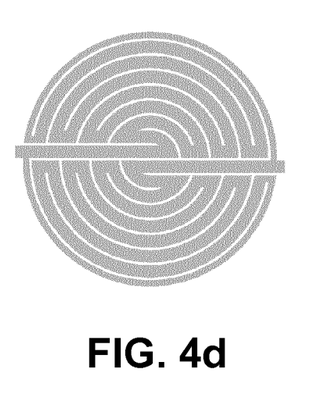

FIGS. 4c and 4d shows heating structure in which the outer tracks 24 are designed to be narrower than the inner tracks 20, connected in series with each other, the ratio inner track width/outer track width being about 2.

The heating structure may be made of one single snail-shaped track, as shown by FIG. 4c.

As shown by FIG. 4d, the heating structure may also be made of several concentric arcs connected in series with each other, forming two parallel wires, each of them heating one half of the active area.

In other embodiments, the tracks may be polygonal.

These designs can be applied to heating structures made of any conducting material that can be patterned by conventional micro-fabrication techniques such as lift-off or photo-lithography and wet or dry etching. Preferably, the heating structure may comprise a material selecting from the group comprising platinum and polysilicon.

The micro-hotplate device of the invention may be used in several sensor types, more particularly in gas sensors, the active layer being chosen according to the use of such sensor.

In some embodiments, the active layer may be a catalytic layer designed to catalyze an exothermic oxidation of combustible gases. The sensors comprising such micro-hotplate device with a catalytic active layer are catalytic gas sensors, also called pellistors or micro-calorimeters, which are used for the detection of combustible gases. The presence of such combustible gases is then detected by measuring the temperature increase induced by the catalyzed exothermal reaction. In this case, as catalytic activity increases with temperature, it is desirable to maximize the temperature of the active layers within the limits of what the whole sensor structure can withstand. The temperature control and temperature uniformity of the active area are crucial. Indeed, in any part of the layer that is below the optimum temperature, the catalytic activity and hence the sensitivity are reduced. Alternatively, any part of the layer that is above the optimum temperature represents hot spots that are harmful to the sensor's stability, reliability, and lifetime.

In some embodiments, the active layer may be a high-emissivity layer designed to form an infrared source. The sensors comprising such micro-hotplate device with said high-emissivity layer are infrared-absorption gas sensors which rely on the absorption of precise infrared wavelengths by certain gases. These sensors utilize small IR sources that can be miniature bulbs or more recently also MEMS-based emitters. The active layer is a high-emissivity layer in order to maximize the light power radiated for a given temperature. Indeed, maximum radiated power is sought in order to reduce the SNR (Signal to Noise Ratio) of the detection system. Since for a grey or black body the radiated power is a function of the forth power of its temperature, it is evident that it is desirable to maximize the emitting layer's temperature in the limits of what the whole emitter structure can stand. Here again, the temperature control and temperature uniformity of the active area are crucial. Indeed, in any part of the active area that is below the optimum temperature, the radiated power is drastically lower, which impacts the SNR and hence the precision of the detection system. And on the other hand, any part of the active area that is above the optimum temperature represents hot spots that are harmful to the sensor's stability, reliability, and lifetime.

In some embodiments, the active layer may be a gas-sensitive layer designed to change its resistivity in the presence of gas. The sensors comprising such micro-hotplate device with said gas-sensitive layer are chemoresistive gas sensors, which are used for example to detect the presence of reducing or oxidizing gases by measuring the change of resistivity of the active layer, usually a pure or doped semiconducting metal oxide, which is deposited on top of the heater but insulated from it by a dielectric layer. In such embodiments, the micro-hotplate device according to the invention further comprises electrodes (not shown in the example of FIGS. 2 and 3) designed to measure the resistance of the active layer. A pair of electrodes is deposited underneath or on top of the active layer. The connecting tracks of these electrodes extend over the membrane from the active area to the rigid frame where they can be used as bonding pads. The influence of the gas on the sensing layer's conductivity is depending on the nature of the active layer, the nature of the gas and the temperature of the active layer. This means that in order to reach optimum selectivity for a given target gas with a given sensing layer the temperature control and temperature uniformity of the active area is crucial. Indeed, in any part of the layer which is not at the optimum temperature, the reaction with the target gas will be lowered and/or the reaction with other gases will be increased, which means that sensitivity and/or selectivity are decreased.

Figure 5:
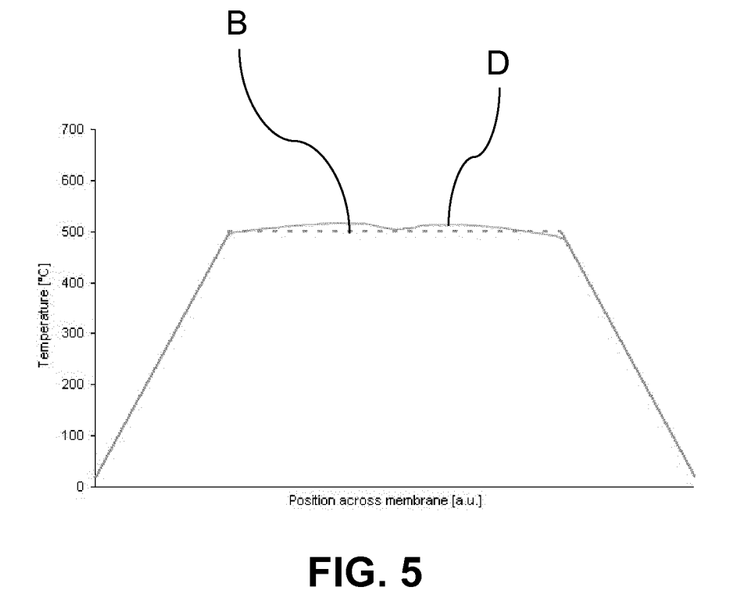
FIG. 5 represents the temperature as a function of the position across the membrane for a micro-hotplate device of the invention, compared to an ideal temperature profile.

FIG. 5 shows a temperature profile (Curve D) measured by optical thermography on a micro-hotplate device of the invention, comprising a platinum heating structure having a pattern similar to the pattern shown by FIG. 4d. This result shows that the micro-hotplate device of the invention produces an excellent temperature uniformity very close to the ideally sought uniform temperature profile (Curve B).

Moreover, in another embodiment, the gas sensor of the invention may further comprise a filtering cap as known from one skilled in the art.

The invention comprises also a method for measuring a concentration of a gas by using a gas sensor comprising a micro-hotplate device as disclosed above, such micro-hotplate device having a heating structure to which at least one heating voltage or at least one heating current is applied to heat the active layer and allow measurement of a concentration of said gas.

According to the invention, said at least one heating voltage or said at least one heating current is supplied intermittently or periodically in cycle mode.

Advantageously, at least one heating voltage or at least one heating current is supplied periodically to the heating structure during an ON-time, at least one rest voltage or at least one rest current is supplied during an OFF-time, said ON-time plus said OFF-time corresponding to a cycle time, the gas concentration being measured during the ON-time. The heating voltages or the heating currents which are supplied during the ON-time may be constant during all the ON-time or may be supplied as heating voltage/current plateau or as heating voltage/current ramp. The rest voltages or the rest currents may be equal to zero, or enough lower than the heating voltages or the heating currents in such a way that the gas sensor doesn't consume any gas or hardly any gas to be detected. The rest voltages or the rest currents which are supplied during the OFF-time may be constant during all the OFF-time or may be supplied as rest voltage/current plateau or as rest voltage/current ramp. The cycle is repeated in loops.

Preferably, the duty cycle corresponding to the ratio ON-time/(ON-time+OFF-time) is comprised between 0.001% and 70%, preferably between 0.02% and 50%, and more preferably between 0.5% and 35%.

Advantageously, the ON-time is comprised between 0.01 second and 2 seconds, the OFF-time being comprised between 1 second and 900 seconds. Preferably, the ON-time is comprised between 0.1 second and 1 second, the OFF-time being comprised between 2 seconds and 15 seconds.

Such cycle mode allows to reduce power consumption, more especially if the gas sensor comprises a filtering cap. Indeed, by taking advantage of the low thermal mass of the micro-hotplate device of the invention and using on the diffusion rate of the gas through the filtering cap, it is possible to achieve reliable measurements with drastic reduction in power consumption compared to the use of the gas sensor in continuous mode. This allows to achieve a large gain in operation lifetime.

The method of the invention for measuring a concentration of a gas is particularly useful for a gas sensor comprising a micro-hotplate device in which the active layer is a catalytic layer designed to catalyze an exothermic oxidation of combustible gases, such as pellistors or micro-calorimeters, which are used for the detection of combustible gases.

EXAMPLES

The following examples illustrate the present invention without however limiting the scope.

A gas sensor according to the invention and comprising a catalytic layer, and a filtering cap was powered with a programmable power supply (TOELLNER TOE0805) where ON-time and OFF-time can be set and cycle repeated in loops. An additional micro-hotplate device which comprises a non-catalytic layer is connected in series and used as a reference. The voltage applied during the ON-time is equal to 3.0 V and the voltage applied during the OFF-time is equal to 0.0 V.

The sensor has been tested under gas at 8 concentrations of $CH_4$ from 0.5% to 4% of $CH_4$/air. The test conditions are: 23° C.; 40% RH, 800 ml/min in PTFE test cell.

The sensor has been tested with three different operation modes:
1. Continuous mode—120 mW
2. 10% duty cycle with 10 seconds cycle length (ON-time=1 s and OFF-time=9 s)—12 mW
3. 1.67% duty cycle with 12 seconds cycle length (ON-time=0.2 s and OFF-time=11.8 s)—2 mW The results are shown by FIG. 6 which represents the output signal corresponding to the sensitivity measured for different concentrations from 0 to 4% $CH_4$ vol./air for:
- a continuous mode with a sensor of the invention without filtering cap, curve A—round dots
- a continuous mode with the same sensor but comprising a conventional filtering cap, curve B—rhombus dots
- 10% duty cycle with 10 seconds cycle length (ON-time=1 s and OFF-time=9 s) with the same sensor comprising a conventional filtering cap, curve C—square dots
- 1.67% duty cycle with 12 seconds cycle length (ON-time=0.2 s and OFF-time=11.8 s) with the same sensor comprising a conventional filtering cap, curve D—triangle dots For examples corresponding to a cycle mode, the output signal corresponding to the sensitivity was measured 200 ms after the start of the ON-time.

Figure 6:
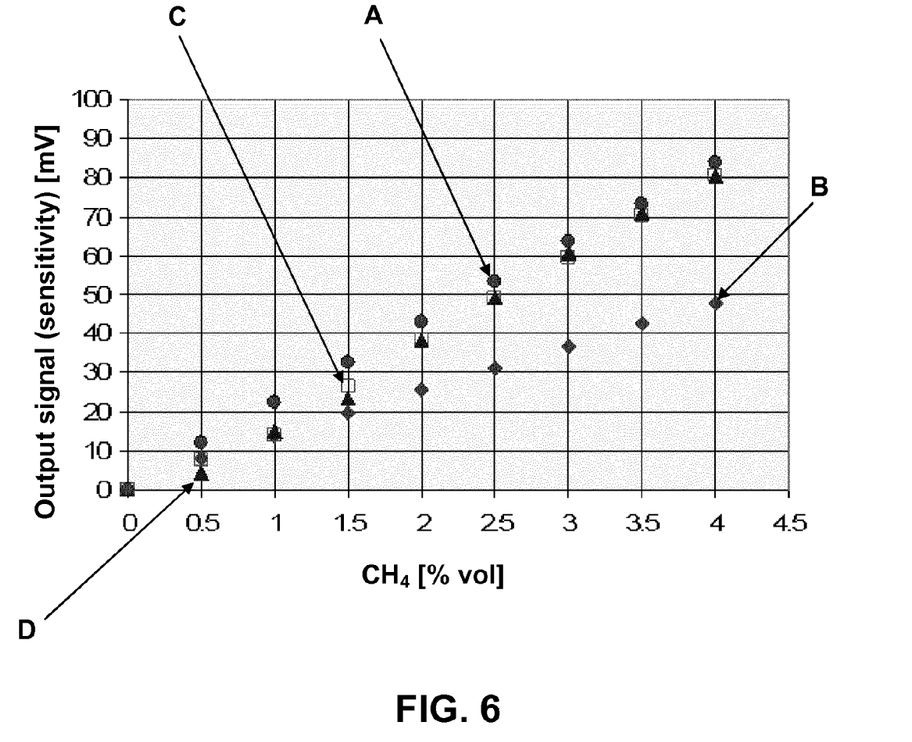
FIG. 6 represents the output signal corresponding to the sensitivity measured for various concentrations of $CH_4$ for different operating modes.

FIG. 6 shows that the method for measuring a concentration of a gas of the invention allows to obtain a sensitivity of the sensor which is higher than in continuous or isothermal mode. Moreover, the method for measuring a concentration of a gas of the invention allows to reduce the sensitivity loss induced by the filtering cap in continuous mode. During the OFF-time, as the gas to be detected is not consumed, its concentration on the sensor side of the filter has time to re-equilibrate itself with the gas concentration to be detected (on the other side of the filter). Thus, right after the start of the ON-time, the gas concentration is maximal, which allows for maximal catalytic reaction and thus maximal sensitivity.

As the cycle mode allows to reduce power consumption, the battery life of the sensor is extended.

Table 1 and table 2 below show the extended battery life for a sensor using a dual AA battery with two different cycle modes:

TABLE 1

| Battery capacity | 2850 | mAh |
|---|---|---|
| Cycle life consideration | 80% | |
| Constant current consumption | 40 | mAh |
| Constant current lifetime | 57 | H |
| Cycle mode | 10% | duty cycle |
| ON-time | 1 | sec. |
| OFF-time | 9 | sec. |
| Period | 10 | sec. |
| Average power | 12 | mW |
| Cycle mode lifetime | 3.4 | Weeks |

Table 1 shows that the battery life of the sensor battery using a duty cycle of 10% according to the invention is extended to more than 3 weeks.

TABLE 2

| Battery capacity | 2850 | mAh |
|---|---|---|
| Cycle life consideration | 80% | |
| Constant current consumption | 40 | mAh |
| Constant current lifetime | 57 | H |
| Cycle mode | 1.67% | duty cycle |
| ON-time | 0.2 | sec. |
| OFF-time | 11.8 | sec. |
| Period | 12 | sec. |
| Average power | 2 | mW |
| Cycle mode lifetime | 20.4 | Weeks |

Table 2 shows that the battery life of the sensor battery using a duty cycle of 1.67% according to the invention is extended to more than 20 weeks.

Table 3 below shows the extended battery life for a safety device comprising a sensor of the invention and requiring a measurement of the gas concentration every second (useful for example for miners) and for a consumer market home detector requiring a measurement of the gas concentration only every quarter-hour.

TABLE 3

| Application | Consumer market home detector (Low cost battery) | Safety device High end product | |
|---|---|---|---|
| Battery capacity | 250 | 1100 | mAh |
| Cycle life consideration | 80% | 80% | |
| PEL Constant current consumption | 40 | 40 | mAh |
| Constant current lifetime | 5 | 22 | H |
| Cycle mode | 0.022% | 20% | duty cycle |
| T_ON | 0.2 | 0.2 | sec. |
| T_OFF | 899.8 | 0.8 | sec. |
| Period | 900 | 1 | sec. |
| Average power | 0.03 | 24 | mW |
| Cycle mode lifetime | 22500 | 110 | Hours |
| Cycle mode lifetime | 938 | 4.6 | days |
| Cycle mode lifetime | 134 | 0.7 | weeks |

Table 3 shows that the battery life of the consumer market home detector using a duty cycle of 0.022% according to the invention is extended from 5 hours to more than 2 years. The battery life of the safety device using a duty cycle of 20% according to the invention is extended from 22 hours to more than 4 days.

The invention claimed is:

1. A micro-hotplate device comprising a frame, a membrane, an active area comprising at least one active layer, and a heating structure designed to heat said active layer, said heating structure having concentric tracks and comprising inner tracks and inner spaces and outer tracks and outer spaces as being the one or two tracks and spaces located the furthest away from the center of the heating structure, wherein said outer tracks are designed to be located closer to their neighboring tracks and/or are designed to have a width which is lower than those of the inner tracks such that the outer tracks are narrower than the inner tracks, the width and the spacing of said inner tracks being substantially constant.

2. The micro-hotplate device according to claim 1, the outer tracks being designed to be located closer to their neighboring tracks, wherein the ratio inner space width/outer space width is higher than 2, and preferably higher than 4.

3. The micro-hotplate device according to claim 2, wherein the ratio inner space width/outer space width is less than 50.

4. The micro-hotplate device according to claim 1, the outer tracks being designed to have a width which is lower than those of the inner tracks, wherein the ratio inner track width/outer track width is higher than 1.3, and preferably higher than 2.

5. The micro-hotplate device according to claim 4, wherein the ratio inner track width/outer track width is less than 5.

6. The micro-hotplate device according to claim 1, wherein the tracks are circular.

7. The micro-hotplate device according to claim 6, wherein the heating structure is made of one single snail-shaped track.

8. The micro-hotplate device according to claim 6, wherein the heating structure is made of several concentric arcs connected in series with each other.

9. The micro-hotplate device according to claim 1, wherein the tracks are polygonal.

10. The micro-hotplate device according to claim 1, wherein the heating structure comprises a material selecting from the group comprising platinum and polysilicon.

11. The micro-hotplate device according to claim 1, wherein the active layer is a catalytic layer designed to catalyze an exothermal oxidation of combustible gases.

12. The micro-hotplate device according to claim 1, wherein the active layer is a high-emissivity layer designed to form an infrared source.

13. The micro-hotplate device according to claim 1, wherein the active layer is a gas-sensitive layer designed to change its resistivity in the presence of gas.

14. The micro-hotplate device according to claim 13, wherein it further comprises electrodes designed to measure the resistance of the active layer.

15. A gas sensor comprising a micro-hotplate device according to claim 13.

16. A gas sensor comprising a micro-hotplate device according to claim 14.

17. The gas sensor according to claim 15, wherein it comprises a micro-hotplate device in which the active layer is a catalytic layer designed to catalyze an exothermal oxidation of combustible gases in order to form a catalytic gas sensor.

18. The gas sensor according to claim 15, wherein it comprises a micro-hotplate device in which the active layer is a high-emissivity layer designed to form an infrared source in order to form an infrared-absorption gas sensor.

19. The gas sensor according to claim 15, wherein it comprises a micro-hotplate device in which the active layer is a gas-sensitive layer designed to change its resistivity in the presence of gas in order to form a chemoresistive gas sensor.

20. A method for measuring a concentration of a gas by using a gas sensor comprising a micro-hotplate device according to claim 1, such micro-hotplate device having a heating structure to which at least one heating voltage or at least one heating current is applied to heat the active layer and allow measurement of a concentration of said gas, wherein said at least one heating voltage or said at least one heating current is supplied intermittently in cycle mode.

21. The method for measuring a concentration of a gas according to claim 20, wherein at least one heating voltage or at least one heating current is supplied periodically to the heating structure during an ON-time, in that at least one rest voltage or at least one rest current is supplied during an OFF-time, said ON-time plus said OFF-time corresponding to a cycle time, the gas concentration being measured during the ON-time.

22. The method for measuring a concentration of a gas according to claim 21, wherein the ratio ON-time/(ON-time+OFF-time) is comprised between 0.001% and 70%, preferably between 0.02% and 50%, and more preferably between 0.5% and 35%.

23. The method for measuring a concentration of a gas according to claim 22, wherein the ON-time is comprised between 0.01 second and 2 seconds, the OFF-time being comprised between 1 second and 900 seconds.

24. The method for measuring a concentration of a gas according to claim 23, wherein the ON-time is comprised between 0.1 second and 1 second, the OFF-time being comprised between 2 seconds and 15 seconds.

* * * * *